(12) United States Patent
  Gattinoni

(10) Patent No.: US 12,678,080 B2
(45) Date of Patent: Jul. 14, 2026

(54) PROBE FOR MEASURING INTRAVESICAL PRESSURE

(71) Applicants: Luciano Gattinoni, Milan (IT); SIDAM S.R.L., Franzione San Giacomo Roncole (IT)

(72) Inventor: Luciano Gattinoni, Milan (IT)

( * ) Notice: Subject to any disclaimer, the term of this patent is extended or adjusted under 35 U.S.C. 154(b) by 17 days.

(21) Appl. No.: 16/091,903

(22) PCT Filed: Apr. 3, 2017

(86) PCT No.: PCT/IB2017/051893
  § 371 (c)(1),
  (2) Date: Oct. 5, 2018

(87) PCT Pub. No.: WO2017/175114
  PCT Pub. Date: Oct. 12, 2017

(65) Prior Publication Data
  US 2019/0110731 A1    Apr. 18, 2019

(30) Foreign Application Priority Data
  Apr. 5, 2016    (IT) ............................... 2016A002329

(51) Int. Cl.
  *A61B 5/20*      (2006.01)
  *A61B 5/00*      (2006.01)
  (Continued)

(52) U.S. Cl.
  CPC ............ *A61B 5/205* (2013.01); *A61B 5/6853* (2013.01); *A61B 6/12* (2013.01); *A61B 90/39* (2016.02);
  (Continued)

(58) Field of Classification Search
  CPC ........... A61B 5/205; A61B 90/39; A61B 6/12; A61B 5/6853; A61B 2090/3966;
  (Continued)

(56) References Cited

U.S. PATENT DOCUMENTS 5,256,141 A * 10/1993 Gencheff .......... A61M 25/0032
                                                      604/501
5,279,551 A * 1/1994 James ................ A61B 17/3415
                                                      604/44

(Continued)

FOREIGN PATENT DOCUMENTS

EP          1255485 A1    11/2002

OTHER PUBLICATIONS

Malbrain, Manu. (2004). Different techniques to measure intra-abdominal pressure (IAP): Time for a critical re-appraisal. Intensive care medicine. 30. 357-71. 10.1007/s00134-003-2107-2 (Year: 2004).*

(Continued)

*Primary Examiner* — Justin Xu
(74) *Attorney, Agent, or Firm* — David B. Tingey; K. Russell Griggs; Kirton McConkie

(57) ABSTRACT

The probe for measuring intravesical pressure includes a flexible tubular element of elongated conformation and having a first extremity comprising at least a supply mouth associable with the supply means of a fluid, a second extremity opposite to the first extremity, positionable inside the bladder of a patient along a direction of insertion, and a first sensing element and at least a second sensing element associated with the tubular element in the proximity of the second extremity and adapted to measure the pressure inside the patient's bladder.

13 Claims, 3 Drawing Sheets

(51) Int. Cl.

| | |
|---|---|
| *A61B 6/12* | (2006.01) |
| *A61B 90/00* | (2016.01) |
| *A61M 25/10* | (2013.01) |

(52) U.S. Cl.
CPC .. *A61M 25/1011* (2013.01); *A61B 2090/3966* (2016.02); *A61M 2025/1015* (2013.01); *A61M 2025/1079* (2013.01)

(58) Field of Classification Search
CPC ...... A61M 25/1011; A61M 2025/1015; A61M 2025/1079
See application file for complete search history.

(56) References Cited

U.S. PATENT DOCUMENTS

| | | | | |
|---|---|---|---|---|
| 5,752,522 A * | 5/1998 | Murphy | .............. | A61B 5/1076 |
| | | | | 600/587 |
| 6,167,886 B1 | 1/2001 | Engel et al. | | |

| | | | | |
|---|---|---|---|---|
| 2008/0097404 A1* | 4/2008 | Yribarren | .............. | A61F 2/958 |
| | | | | 623/1.34 |
| 2010/0113939 A1* | 5/2010 | Mashimo | ........ | A61M 25/10187 |
| | | | | 600/488 |
| 2010/0268159 A1* | 10/2010 | Engel | ...................... | A61L 29/18 |
| | | | | 156/60 |
| 2010/0280451 A1* | 11/2010 | Teeslink | ........... | A61B 17/12109 |
| | | | | 604/99.04 |
| 2014/0012235 A1 | 1/2014 | Pinchuk et al. | | |
| 2015/0335866 A1* | 11/2015 | Stapleton | .......... | A61M 25/1034 |
| | | | | 604/103.1 |

OTHER PUBLICATIONS

International Search Report and Written Opinion dated Jun. 7, 2017 from International Patent Application No. PCT/IB2017/051893 filed Apr. 3, 2017.

* cited by examiner

PROBE FOR MEASURING INTRAVESICAL PRESSURE

TECHNICAL FIELD

The present invention relates to a probe for measuring intravesical pressure.

BACKGROUND ART

In the medical field, the measuring of intravesical pressure is an important parameter for assessing the clinical situation of a number of abdominal illnesses and complications related thereto.

In particular, the evaluation of the intravesical pressure is fundamental as a correlative parameter in the study of the pathogenesis of intra-abdominal organs, or in the case of illnesses such as, for example, cirrhosis of the liver, intestinal diseases, or in post-operation phase following abdomen surgery.

In medical practice, the relief of intravesical pressure occurs through the use of vesical catheters, the most popular of which are the Foley type catheters.

The Foley catheter comprises a flexible tubular element with elongated shape, with a first extremity provided with a supply mouth associable with means for supplying a fluid, and a second extremity positionable inside the bladder of a patient and provided with an inflatable balloon.

The second extremity is positioned inside the patient's bladder and is provided with an inflatable balloon adapted to block the second extremity itself inside the bladder and, at the same time, to measure its pressure values.

In use, after positioning the second extremity inside the patient's bladder and inflating the balloon with water, the bladder is emptied and then filled with a physiological saline solution.

After terminating the emptying of the bladder, the catheter is isolated from the outside before being reconnected to a physiological saline solution collection tank for the entry of the physiological saline solution inside the bladder itself.

At the end of such operations, the catheter is then disconnected from the collection tank and connected to pressure measuring means, of the type of a transducer or the like, adapted to measure the pressure gradient and relative variations according to the external stimulations received by the bladder.

Nevertheless, the above type of catheter has a number of drawbacks including the fact that the presence of just one inflatable balloon, in the event of the latter inflating in an off-center way with respect to the tubular element or accidentally adhering to the walls of the bladder, falsifies the measured pressure data, thereby cancelling the truthfulness of the clinical study.

Furthermore, such known catheters require the bladder to be emptied and subsequently filled with a physiological saline solution, thus considerably increasing the risk of bacterial contamination and, therefore, the occurrence of infections at vesical level.

To this must be added the fact that the aforementioned steps of emptying and subsequent filling of the bladder call for in succession the connection and the disconnection of the catheter to/from the relative supply and subsequent monitoring means; besides extending work time, this also prevents measuring the pressure data in continuous mode.

DESCRIPTION OF THE INVENTION

The main aim of the present invention is to provide a probe for measuring intravesical pressure which allows measuring the pressure gradient at the physiological state of the bladder, and i.e., eliminating the need to empty the bladder and subsequently refill it with a solution which, despite being physiological, is exogenous to the patient's body.

Another object of the present invention is to provide a probe for measuring intravesical pressure which allows measuring the pressure data in continuous mode, thus eliminating the need to connect and disconnect the catheter to/from the relative supply and monitoring means, considerably reducing the risk of infections at vesical level.

Yet another object of the present invention is to provide a probe for measuring intravesical pressure which ensures the truthfulness of the measured pressure data.

A further object of the present invention is to provide a probe for measuring intravesical pressure which allows to overcome the mentioned drawbacks of the prior art within the ambit of a simple, rational, easy, effective to use and low cost solution.

The above mentioned objects are achieved by the present probe for measuring intravesical pressure according to claim 1.

BRIEF DESCRIPTION OF THE DRAWINGS

Other characteristics and advantages of the present invention will become more evident from the description of a preferred, but not exclusive, embodiment of a probe for measuring intravesical pressure, illustrated by way of an indicative, but non-limiting example in the accompanying drawings, wherein.

EMBODIMENTS OF THE INVENTION

Figure 1:
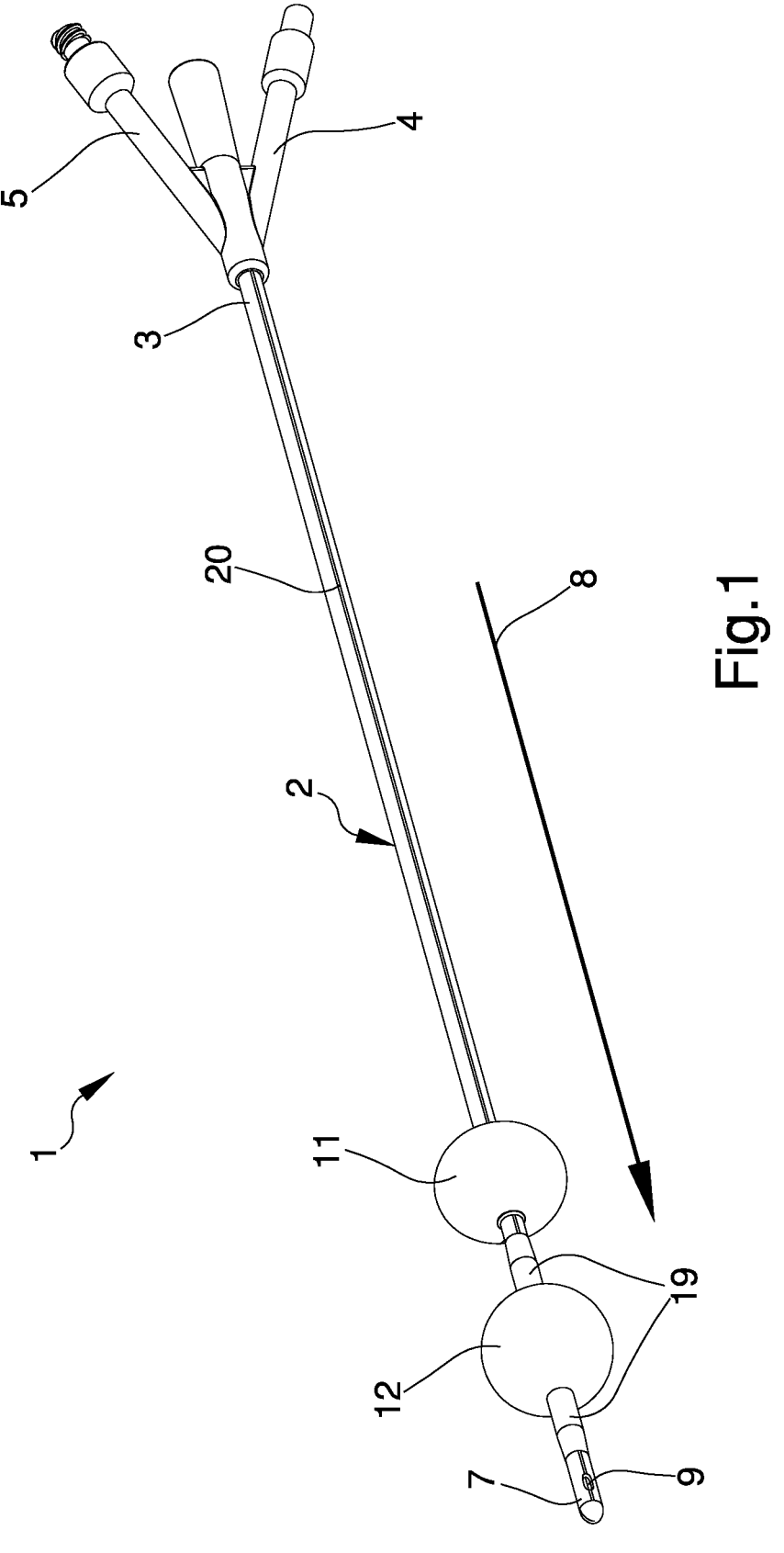
FIG. 1 is an axonometric view of the probe according to the invention in a first embodiment.
Figure 2:
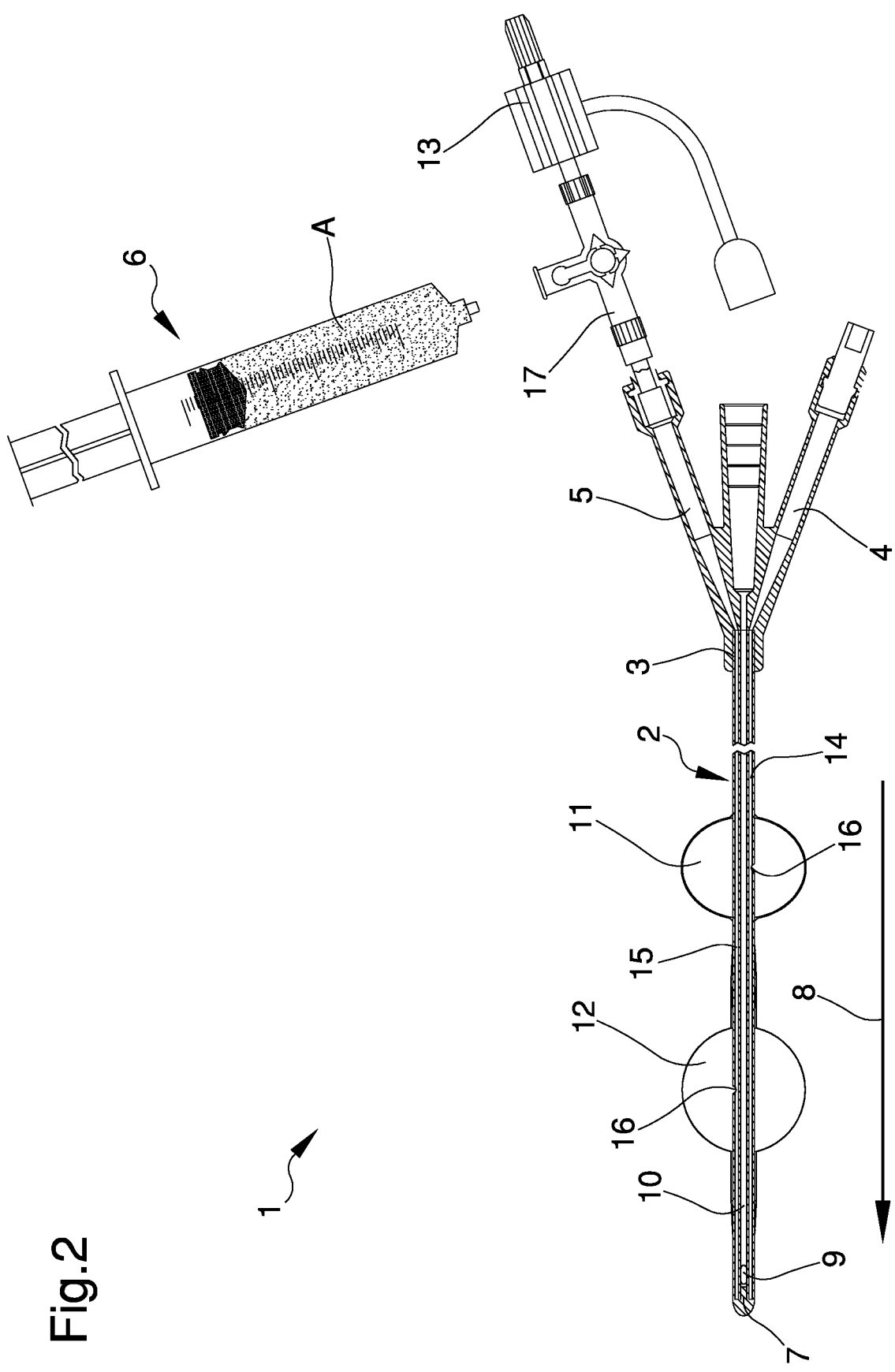
FIG. 2 is a sectional view of the probe of FIG. 1.

With particular reference to such figures, globally indicated with reference numeral 1 is a probe for measuring intravesical pressure.

The probe 1 comprises a flexible tubular element 2 of elongated conformation. The tubular element 2 is made of elastic and flexible material, of the PVC, polyurethane type or the like, and which is insertable, at least in part, through the urethra and as far as a patient's bladder.

Furthermore, the tubular element 2 has a first extremity 3 comprising a supply mouth 4, 5 associable with the supply means 6 of a fluid A.

It is well to underline that by the term "fluid" is meant any substance or mix of substances which deforms without limitation if it undergoes external stresses and, irrespective of the entity of the latter, reference is made to a state of matter which comprises substances in both gaseous and liquid state.

Preferably, the fluid is water or air.

The tubular element 2 has a second extremity 7 positionable inside the bladder of a patient along a direction of insertion 8.

As can be seen in the illustrations, the second extremity 7 is connected in a semi-sphere fashion to prevent any injury to the patient during operations of insertion of the second extremity itself inside the bladder and is made, at least in part, of radio-opaque material.

In particular, the second extremity 7 comprises a dispensing hole 9 communicating with a transit duct 10 passing through the tubular element 2 and adapted to allow the transit of substances, e.g., pharmacological and/or lubricating substances, or alternatively, to permit the extraction of biological residues from inside the patient's bladder.

According to the invention, the probe 1 comprises at least a first sensing element 11 and at least a second sensing element 12 associated with the tubular element 2 in the proximity of the second extremity 7 and adapted to measure the pressure inside the patient's bladder.

Advantageously, at least one of the first sensing element 11 and the second sensing element 12 comprises an inflatable balloon.

In particular, the first sensing element 11 comprises a first balloon for locking the second extremity 7 inside the patient's bladder.

Similarly, the second sensing element 12 comprises a second balloon for measuring the pressure inside the patient's bladder.

Both the balloons 11, 12 are made of elastic and soft polymer material, suitable both for the insertion inside the patient's bladder and for measuring slight pressure changes.

Advantageously, at least one of the first balloon 11 and the second balloon 12 comprises polyolefins.

In detail, the first balloon 11 is made of silicone.

At the same time, the second balloon 12 is made of polyolefins.

With reference to the particular embodiment shown in the illustrations, the first balloon 11 is arranged upstream of the second balloon 12 with respect to the direction of insertion 8.

Alternative embodiments cannot however be ruled out in which the first balloon 11 is arranged downstream of the second balloon 12 with respect to the direction of insertion 8 of the probe 1.

In order to measure the changes in pressure inside the bladder, at least one of the first sensing element 11, i.e. the first balloon, and the second sensing element 12, i.e. the second balloon, is associated with monitoring means 13 of the detected pressure measurements.

The balloons 11, 12 have two openings at their extremities substantially opposite one another, inside which is inserted, hydraulically sealed, a section of the tubular element 2.

The connection between the balloons 11, 12 and the monitoring means 13 or the supply means 6 takes place by means of communication channels 14, 15 with which the tubular element 2 is equipped.

In this case, the tubular element 2 has a first communication channel 14 between the first balloon 11 and the supply mouth 4, 5.

Similarly, the tubular element 2 has a second communication channel 15 between the second balloon 12 and the supply mouth 4, 5.

Advantageously, in correspondence of the balloons 11, 12, the tubular element 2 has a communication hole 16 with the first communication channel 14 and with the second communication channel 15, respectively.

As can be seen in the figures, the supply mouth 4, 5 comprises a first portion 4 associated with the supply means 6 and a second portion 5 associated with a connecting element 17 for the alternate connection of the second balloon 12 to the supply means 6 or to the monitoring means 13.

Preferably, the first portion 4 and the second portion 5 have non-return valves adapted to keep the balloons 11, 12 inflated.

The supply means 6 comprise a device for supplying the fluid A, e.g., of the syringe type, and are adapted to inflate the first balloon 11 until the pre-established size is reached for blocking the tubular element 2 inside the patient's bladder and, similarly, they are adapted to inflate the second balloon 12 with a pre-established volume of fluid A dependent on the size of the patient's bladder or on particular clinical requirements tied to the clinical situation of the patient. The monitoring means 13 comprise a transducer device for the pressures measured outside the balloons 11, 12 connectable to means of displaying such pressure measurements, not shown in the illustrations.

Preferably, the connecting element 17 is of the type of a three-way tap which can be operated manually and which permits connecting, alternatively, the second balloon 12 to the syringe 6 or to the transducer device 13.

In this case, the first portion 4 is communicating with the first communication channel 14 for inflating the first balloon 11, and the second portion 5 is associated with the second communication channel 15 for inflating the second balloon 12 with a predefined volume of the fluid A, and for connecting to the monitoring means 13.

Figure 3:
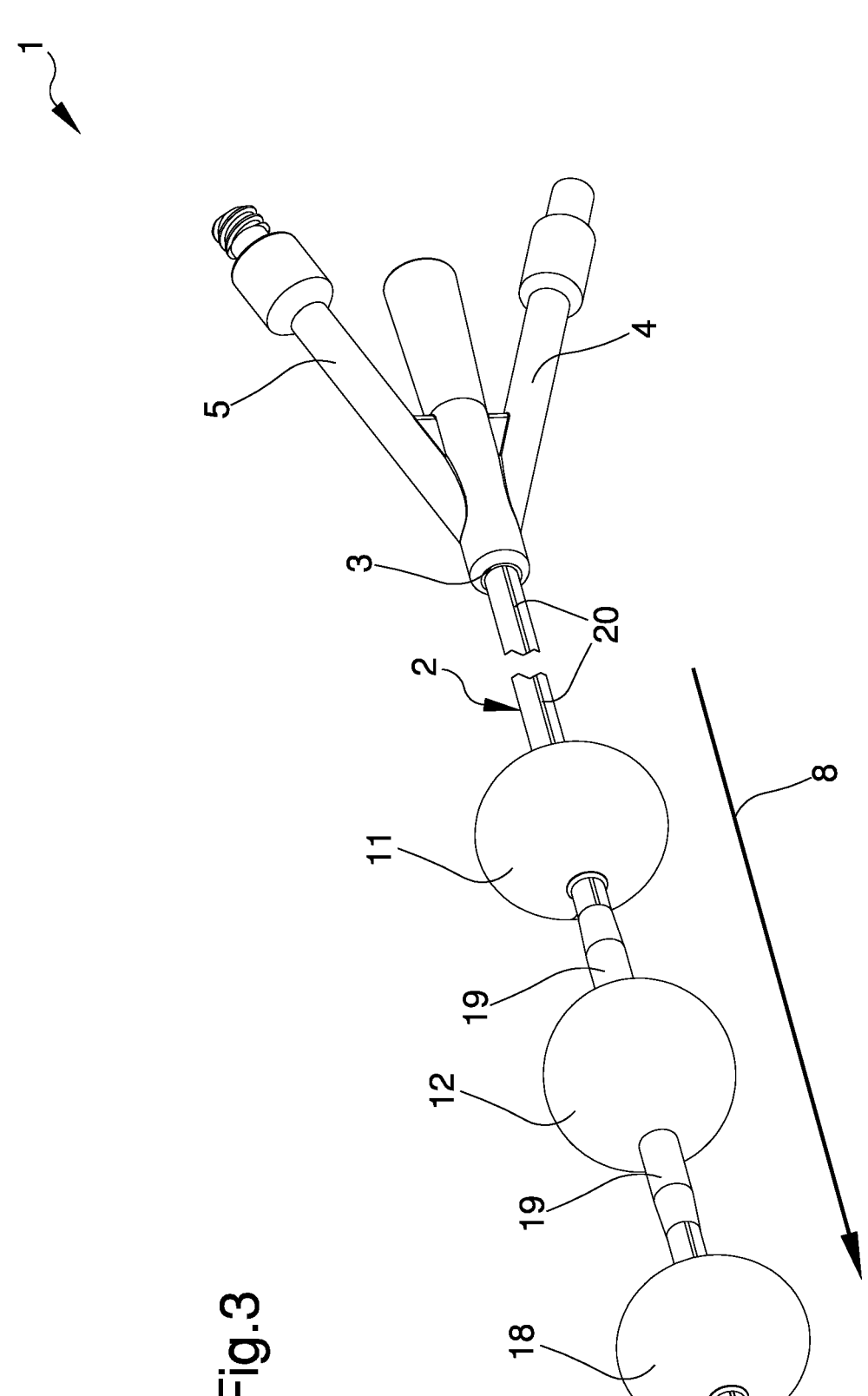
FIG. 3 is an axonometric view of the probe according to the invention in a second embodiment.

FIG. 3 shows a second embodiment of the probe 1, the structural characteristics of the tubular element 2 and of the supply mouth 4, 5 are similar to those described in the previous embodiment, to the detailed description of which reference is made in its entirety.

Unlike what happened before, the probe 1 comprises a third balloon 18 for locking.

In the present case, the third balloon 18 is arranged downstream of the second balloon 12 with respect to the direction of insertion 8.

The presence of the third balloon 18 is intended to ensure the maintenance of the second balloon 12 in a symmetrical and centered position with respect to the tubular element 2.

In other words, in the case of the second extremity 7 of the tubular element 2 suffering any deviation tied to any asymmetric and off-center inflation of one of the balloons 11, 12, the presence of the third balloon 18 aims at ensuring the symmetry and centering of the second balloon 12 designated to measuring the pressure values.

Advantageously, the third balloon 18 is communicating with the first communication channel 14; in the present case, the tubular element 2 has a respective communication hole 16 with the first communication channel 14.

This allows the simultaneous inflation of the first balloon 11 and of the third balloon 18.

Alternative embodiments cannot however be ruled out in which the tubular element 2 has a third communication channel between the third balloon 18 and the supply means 6, in such a way as to allow the independent inflation of the first balloon 11 and the third balloon 18.

Furthermore, the probe 1 comprises marker means 19, 20 for marking the position of the probe itself which are made of radiopaque material and are viewable by means of radiography.

The marker means 19, 20 are made in the proximity of the extremities of the balloons 11, 12.

In practice, the presence of such marker means 19, 20 permits viewing, by means of radiography, during and after insertion, the position of the tubular element 2 inside the urethra and bladder of the patient.

The aforementioned marker means 19, 20 comprise a substantially cylindrical single body piece 19 associated with the tubular element 2.

Nevertheless, alternative embodiments cannot be ruled out in which the marker means 19, 20 are made in the form of windings made by means of tungsten filaments or the like, wound around respective sections of the extremities of the balloons 11, 12.

Furthermore, the marker means 19, 20 comprise a track 20 in radio-opaque material which extends longitudinally along the entire tubular element 2.

The operation of the present embodiment is as follows.

The tubular element 2 is inserted by a medical operator through the urethra as far as the patient's bladder. It is best to point out that the patient's bladder is in the physiological state, i.e., partially or totally full, and does not require draining operations.

Such insertion can be made by placing the first balloon 11 and the second balloon 12 inside the patient's bladder, and in particular by positioning the second balloon 12 in such a way that it is substantially centred with respect to the bladder.

In other words, by controlling the position of the marker means 19, 20 by means of radiography it is possible to check the correct positioning of the second balloon 12 so that it does not adhere to the inner walls of the bladder.

Subsequently, the balloon 11 and the balloon 18, if any, are inflated by associating the syringe 6 to the first portion 4.

At the same time, the tap 17 is positioned in such a way as to put in communication the second communication channel 15 with the syringe 6 associated with the connecting element 17.

The second balloon 12 is therefore inflated with a pre-defined volume of fluid A. At this point, the medical operator positions the tap 17 in such a way as to put in communication the second communication channel 15, that is, the second balloon 12, with the transducer device 13.

The medical operator can therefore check the pressure values measured by the transducer device 13; more specifically, the transducer device 13 measures the pressure values according to the external stimulations which the second balloon 12 receives and which affect the fluid A contained inside it.

It has in practice been ascertained that the described invention achieves the intended objects.

The fact is underlined that the particular solution of providing a first balloon for blocking the tubular element inside the bladder and a second sensing balloon associated with a connecting element permits measuring the pressure data in continuous mode, eliminating the need to connect and disconnect the probe from the corresponding supply and monitoring means, thus resulting in a considerable reduction in the risk of infections at bladder level.

To this must be added the fact that the presence of at least two balloons ensures the pressure data sensing balloon to be kept in the centring and symmetry position with respect to the tubular element, thus ensuring the truthfulness of the measured data.

The invention claimed is:

1. A probe for measuring intravesical pressure within a bladder of a patient, wherein the probe measures a physiological state of the bladder and therefore eliminates a need to empty the bladder and subsequently fill the bladder with a solution prior to positioning and use of the probe, the probe comprising:

a flexible tubular element of elongated conformation and having:

a first extremity comprising a supply mouth associable with a supply means of a fluid; and a second extremity opposite to the first extremity, positionable inside a partially or totally full bladder of a patient along a direction of insertion, the second extremity comprising a radiopaque semi-spherical shape to prevent injury to the patient during insertion of the second extremity;

wherein the probe comprises a first sensing element and a second sensing element associated with the flexible tubular element in proximity of the second extremity, wherein at least one of the first sensing element and the second sensing element is used to measure a pressure inside a bladder of the patient, wherein the first sensing element comprises a first balloon for locking the second extremity inside the patient's bladder, the flexible tubular element having a first communication channel between the first balloon and the supply mouth, wherein the second sensing element comprises a second balloon for measuring the pressure inside the patient's bladder, the flexible tubular element having a second communication channel between the second balloon and the supply mouth, wherein the first extremity further comprises a first portion that is configured to be in fluid communication with the supply means and a second portion that is configured to be in fluid communication with a connecting element for an alternate connection of the second balloon to at least one of: (a) the supply means and (b) monitoring means for detecting pressure measurements, wherein the probe comprises a third balloon that is configured to ensure a maintenance of the second balloon in a symmetrical and centered position with respect to the flexible tubular element, wherein at least one of the first balloon, the second balloon, and the third balloon has an opening at an extremity that is hydraulically sealed to a portion of the flexible tubular element, and wherein the probe further comprises marker means for marking a position of the probe by radiography, and where the marker means comprise a non-circumferential marker in radio-opaque material that extends longitudinally along the flexible tubular element, wherein the marker means further includes tungsten filament windings that abut proximal and distal extremities of the second balloon, wherein the first portion has a first non-return valve and the second portion has a second non-return valve, wherein the first non-return valve and the second non-return valve are respectively used to (i) keep the first balloon inflated until a pre-established size is reached for blocking the tubular element inside the patient's bladder and (ii) responsive to a determination by the monitoring means that the first balloon is inflated to the pre-established size, inflate the second balloon with a pre-established volume of fluid dependent on at least one of (a) a size of a portion of the patient's bladder and (b) on a particular clinical requirement tied to a clinical situation of the patient, and wherein the first portion is in fluid communication with the first communication channel for inflating the first balloon and the third balloon, and the second portion is associated with the second communication channel for inflating the second balloon with the pre-established volume of fluid, and for connecting to the monitoring means for detecting pressure measurements, the monitoring means for detecting pressure measurements comprising a transducer device for pressures measured outside the first balloon, the second balloon, and the third balloon, and with the monitoring means for detecting pressure measurements being connectable to means of displaying such pressure measurements.

2. The probe according to claim 1, wherein at least one of the first sensing element and the second sensing element is associated with the monitoring means for detecting pressure measurements.

3. The probe according to claim 1, wherein at least one of the first balloon and the second balloon comprises at least one polyolefin.

4. The probe according to claim 1, wherein the first balloon is arranged upstream of the second balloon with respect to the direction of insertion.

5. The probe according to claim 1, wherein, in correspondence of the first balloon and the second balloon, the flexible tubular element defines a first communication hole with the first communication channel and a second communication hole with the second communication channel.

6. The probe according to claim 1, wherein the third balloon is arranged downstream of the second balloon with respect to the direction of insertion.

7. The probe according to claim 1, wherein the non-circumferential marker comprises a track in radio-opaque material.

8. The probe according to claim 7, wherein the marker means further includes a circumferential marker in radio-opaque material adjacent to at least one extremity of the first balloon or the second balloon.

9. The probe according to claim 1, wherein the flexible tubular element comprises a third communication channel between the third balloon and the supply mouth to allow for inflation of the first balloon independent from the third balloon.

10. A probe for measuring intravesical pressure within a bladder of a patient, wherein the probe measures a physiological state of the bladder and therefore eliminates a need to empty the bladder and subsequently fill the bladder with a solution prior to positioning and use of the probe, the probe comprising:

a flexible tubular element of elongated conformation and having:

a first extremity comprising a supply mouth associable with a supply means of a fluid and comprising a first portion that is configured to be in fluid communication with the supply means and a second portion that is configured to be in fluid communication with a connecting element for an alternate connection of a sensing balloon to at least one of: (a) the supply means and (b) monitoring means for detecting pressure measurements; and a second extremity opposite to the first extremity, positionable inside a bladder in a physiological state of a patient along a direction of insertion, the second extremity comprising a radiopaque semi-spherical shape to prevent injury to the patient during insertion of the second extremity;

wherein the probe comprises a first sensing element and a second sensing element associated with the flexible tubular element in proximity of the second extremity, wherein at least one of the first sensing element and the second sensing element is used to measure a pressure inside a bladder of the patient, wherein the first sensing element comprises a first locking balloon for locking the second extremity inside the bladder of the patient, the flexible tubular element having a first communication channel between the first locking balloon and the supply mouth, wherein the second sensing element comprises the sensing balloon for measuring the pressure inside the patient's bladder, the flexible tubular element having a second communication channel between the sensing balloon and the supply mouth, wherein the probe comprises a second locking balloon that is configured to ensure a maintenance of the sensing balloon in a symmetrical and centered position with respect to the tubular element, the flexible tubular element having a third communication channel between the second locking balloon and the supply mouth to allow for inflation of the first locking balloon independent from the second locking balloon, and wherein the first portion and the second portion have non-return valves used to respectively keep the first locking balloon inflated until a pre-established size is reached for blocking the flexible tubular element inside the patient's bladder and, responsive to a determination by the monitoring means that the first locking balloon is inflated to the pre-established size, to inflate the sensing balloon with a pre-established volume of fluid dependent on at least one of (i) a size of a portion of the patient's bladder and (ii) a particular clinical requirement tied to a clinical situation of the patient, and wherein the first portion is in fluid communication with the first communication channel for inflating the first locking balloon, and the second portion is associated with the second communication channel via the connecting element for inflating the sensing balloon with the pre-established volume of fluid, and for connecting to the monitoring means for detecting pressure measurements, the connecting element being of a type of three-way tap that permits selectively connecting the sensing balloon to at least one of the supply means and the monitoring means for detecting pressure measurements, the monitoring means for detecting pressure measurements comprising a transducer device for pressures measured outside the first locking balloon, the sensing balloon, and the second locking balloon, and with the monitoring means for detecting pressure measurements being connectable to means of displaying such pressure measurements, wherein the probe comprises a marking system for marking a position of the probe that includes (i) a non-circumferential marker in radio-opaque material that extends longitudinally along the entire flexible tubular element and (ii) a circumferential marker in radio-opaque material that is disposed adjacent to at least one extremity of the sensing balloon, wherein the probe further comprises a marker means made in the form of tungsten windings abutting proximal and distal extremities of the sensing balloon.

11. A probe for measuring intravesical pressure within a bladder of a patient, wherein the probe measures a physiological state of the bladder and therefore eliminates a need to empty the bladder and subsequently fill the bladder with a solution prior to positioning and use of the probe, the probe comprising:

a flexible tubular element of elongated conformation and having:

a first extremity comprising a supply mouth associable with a supply means of a fluid and comprising a first portion that is configured to be in fluid communication with the supply means and a second portion that is configured to be in fluid communication with a connecting element for an alternate connection of a second balloon to at least one of: (a) the supply means and (b) monitoring means for continuous detecting of pressure measurements, a second extremity opposite to the first extremity, positionable inside a bladder in a physiological state of a patient along a direction of insertion, the second extremity comprising a radiopaque semi-spherical shape to prevent injury to the patient during insertion of the second extremity;

wherein the probe comprises a first sensing element and a second sensing element associated with the flexible tubular element in proximity of the second extremity, wherein at least one of the first sensing element and the second sensing element is used to measure a pressure inside a bladder of the patient, wherein the first sensing element comprises a first balloon for locking the second extremity inside the patient's bladder, the flexible tubular element having a first communication channel between the first balloon and the supply mouth, wherein the second sensing element comprises the second balloon for measuring the pressure inside the patient's bladder, the flexible tubular element having a second communication channel between the second balloon and the supply mouth, wherein the probe comprises at least a third balloon configured to ensure a maintenance of the second balloon in a symmetrical and centered position with respect to the flexible tubular element, wherein at least one of the first balloon, the second balloon, and the third balloons has a plurality of openings that are hydraulically sealed to the flexible tubular element, wherein the first portion and the second portion respectively have a first non-return valve and a second non-return valve that are respectively used to: (i) keep the first balloon inflated until a pre-established size is reached for blocking the flexible tubular element inside the patient's bladder and (ii) responsive to a determination by the monitoring means that the first balloon is inflated to the pre-established size, inflate the second balloon with a pre-established volume of fluid dependent on at least one of (A) a size of a portion of the patient's bladder and (B) a particular clinical requirement tied to a clinical situation of the patient, wherein the first portion is communicating with the first communication channel for inflating the first balloon and the third balloon, and the second portion is associated with the second communication channel via the connecting element for inflating the second balloon with the pre-established volume of fluid and for connecting to the monitoring means for continuous detecting of pressure measurements, the connecting element being of a type of three-way tap which permits connecting, alternatively, the second balloon to supply means or to the monitoring means for continuous detecting of pressure measurements, and wherein the first and the third balloons are configured to be inflated firstly and simultaneously, the three-way tap is configured to be positioned in such a way as to put in communication the second communication channel with the supply means associated with the connecting element, the second balloon being then configured to be inflated with the preestablished volume of fluid and the three-way tap is further configured to be positioned in such a way as to put in communication the second balloon with the monitoring means for continuous detecting of pressure measurements, the monitoring means for continuous detecting of pressure measurements comprising a transducer device for pressures measured outside the first balloon, the second balloon, and the third balloon, and with the monitoring means for continuous detecting of pressure measurements being connectable to means of displaying such pressure measurements, wherein the probe comprises a radio-opaque marker system for marking a position of the probe, the marker system comprising a circumferential radio-opaque marker disposed adjacent to at least one extremity of the second balloon, and a non-circumferential radio-opaque marker that comprises a track in radio-opaque material that extends longitudinally along an entire length of the tubular element, wherein probe further includes a marker means that includes tungsten filament windings that abut proximal and distal extremities of the second balloon.

12. The probe according to claim 11, wherein the flexible tubular element comprises a third communication channel between the third balloon and the supply mouth to allow for inflation of the first balloon independent from the third balloon.

13. A probe for measuring intravesical pressure within a bladder of a patient, wherein the probe measures a physiological state of the bladder and therefore eliminates a need to empty the bladder and subsequently fill the bladder with a solution prior to positioning and use of the probe, the probe comprising:

a flexible tubular element of elongated conformation comprising:

a first extremity having a supply mouth associable with a supply means of a fluid; and a second extremity opposite to the first extremity, positionable inside a bladder in a physiological state of a patient along a direction of insertion, the second extremity comprising a radiopaque semi-spherical shape to prevent injury to the patient during insertion of the second extremity;

wherein the probe comprises a first sensing element and a second sensing element associated with the flexible tubular element in proximity of the second extremity, wherein at least one of the first sensing element and the second sensing element is used to measure a pressure inside a bladder of the patient, wherein the first sensing element comprises a first balloon for locking the second extremity inside the patient's bladder, the flexible tubular element having a first communication channel between the first balloon and the supply mouth, wherein the second sensing element comprises a second balloon for measuring the pressure inside the patient's bladder, the flexible tubular element having a second communication channel between the second balloon and the supply mouth, and wherein at least one of the first balloon and the second balloon is hydraulically sealed, wherein the first extremity further comprises a first portion that is configured to be in fluid communication with the supply means and a second portion that is configured to be in fluid communication with a connecting element for an alternate connection of the second balloon to at least one of: (a) the supply means and (b) monitoring means for detecting pressure measurements; and wherein the probe further comprises a marker system for marking a position of the probe by radiography, the marker system comprising (i) a non-circumferential marker in radio-opaque material that extends longitudinally along the length of the tubular element, (ii) a circumferential marker in radio-opaque material that is disposed adjacent to an extremity of the first balloon, and (iii) a circumferential marker in radio-opaque material comprising tungsten windings that are disposed adjacent to and abut against an extremity of the second balloon.

* * * * *